United States Patent [19]
Latham, Jr. et al.

[11] Patent Number: 5,494,592
[45] Date of Patent: Feb. 27, 1996

[54] APHERESIS APPARATUS AND METHOD

[75] Inventors: Allen Latham, Jr., Jamaica Plain; Glen E. Jorgensen, Marlborough; Theodoor H. S. Sibinga, Boston; Joseph R. Plante, Millis; Tracey E. Knapp, Hanover, all of Mass.

[73] Assignee: Haemonetics Corporation, Braintree, Mass.

[21] Appl. No.: 372,890

[22] Filed: Jan. 13, 1995

Related U.S. Application Data

[63] Continuation of Ser. No. 53,734, Apr. 27, 1993, abandoned.

[51] Int. Cl.$^6$ .......................... A61M 37/00; B01D 21/26
[52] U.S. Cl. .......................... 210/805; 210/782; 210/789; 604/4; 604/5; 604/6; 494/37
[58] Field of Search .................... 210/782, 789, 210/805; 604/4, 5, 6; 494/37

[56] References Cited

U.S. PATENT DOCUMENTS

| | | | |
|---|---|---|---|
| 3,145,713 | 8/1964 | Latham | 604/4 |
| 3,957,197 | 5/1976 | Sartory et al. | |
| 4,416,654 | 11/1983 | Schoendorfer et al. | 494/10 |
| 4,464,167 | 8/1984 | Schoendorfer et al. | 604/6 |
| 4,675,117 | 6/1987 | Neumann et al. | 210/789 |
| 4,990,132 | 2/1991 | Unger et al. | 604/6 |
| 5,141,645 | 8/1992 | Shiraki et al. | 210/513 |
| 5,370,802 | 12/1994 | Brown | 210/782 |

FOREIGN PATENT DOCUMENTS

| | | |
|---|---|---|
| 0155684 | 3/1985 | European Pat. Off. |
| WO87/06472 | 11/1987 | WIPO |

OTHER PUBLICATIONS

MCS Disposables, Users Manual for the Mobile Collection Systems, Haemonetics Corporation; pp. 4-1-4-5 (Jan., 1992).
Users Manual for Haeomonetics V50 Plus Apheresis System, pp. 1-4-1-6 (May, 1991).
Users Manual for Haemonetics V50 Plus Apheresis System—Extended Storage Platelets (ESP) Protocol Non–Time Saver, pp. 1-3, (May, 1991).
Schoendorfer et al., "The Surge Technique: A Method to Increase Purity of Platelet Concentrates Obtained by Centrifugal Apheresis," Transfusion 23: 182-189 (1983).
Smit Sibinga, Study Reports on Blood: "Fluid Dynamics in a Bowl," Haemonetics, (Apr., 1991).

*Primary Examiner*—John Kim
*Attorney, Agent, or Firm*—Cesari and McKenna

[57] ABSTRACT

An apheresis apparatus and method is disclosed for increasing the purity and yield of platelets separated from donated whole blood in a centrifuge. The whole blood in the centrifuge is diluted by recirculating fluid, such as plasma or saline, at a first flow rate, to mix with further withdrawn whole blood prior to entering the centrifuge. As plasma is collected, it is recirculated through the centrifuge at a second flow rate to further improve the separation between the intermediate density components, i.e., platelets and white blood cells in the "buffy coat." The plasma is then recirculated through the centrifuge at a third flow rate and platelets are displaced out of the centrifuge while the plasma is recirculating through the centrifuge at the third flow rate.

30 Claims, 11 Drawing Sheets

APHERESIS APPARATUS AND METHOD

This application is a continuation of U.S. patent application Ser. No. 08/053,734 filed Apr. 27, 1993, which is abandoned.

BACKGROUND OF THE INVENTION

With the advance Of medical science, the demand for platelet concentrates with low contamination of white blood cells (WBC), such as, lymphocytes is rapidly growing. Platelets are fragments of a large cell located in the marrow called a megakaryocyte. Platelets have no nucleus and are primarily responsible for hemostasis, although they also have a role in tissue healing. They interact to chemicals released from damaged endothelial cells by becoming "sticky" and adhering to the damaged tissue. Platelets then release ADP, a chemical, which causes other platelets to stick to each other. This action, also known as aggregation, forms the primary white clot. Platelets then activate plasma proteins responsible for clotting which produce the "red" clot or the stable clot. Platelets have a half-life of 4–6 days in the normal adult. Normal platelet counts are 150,000–400,000/mm$^3$ in the adult. Platelet counts under 20,000/mm$^3$ can result in spontaneous bleeding.

With the improvement in cancer therapy patients are requiring increased platelet support. In addition, with the large number of screening tests employed for blood products, the number of units that are acceptable are less than in past years. The donor pool is reduced and therefore, the supply of random donor platelets must be conserved.

Procedures for collection of specific blood components from a single blood donor, apheresis, is proven to be a satisfactory approach to cover the demand for blood components. Recently, the equipment for collection of platelets has been directed towards maximizing the yield of pure platelets. (See for example, U.S. Pat. No. 4,416,654.) Today, it is understood that the contamination of platelet concentrates by WBC can lead to medical complications, such as graft-versus-host reactions.

Current blood separation equipment for the collection of platelet concentrates are not sufficient for automatically collecting an optimum pure platelet concentrate.

Accordingly, there is a continuing need for an apheresis separation apparatus and method for automatically collecting platelet concentrates with low white blood cell contamination while maximizing platelet yields.

SUMMARY OF THE INVENTION

The present invention provides a pheresis apparatus and method for increasing blood component yield from donated whole blood in a centrifugation fractionation volume. In accordance with the invention, whole blood is diluted by recirculating lower density fluid, preferably plasma, at a first flow rate, to mix with further withdrawn whole blood prior to entering the centrifuge. The diluted whole blood enters the fractionation or separation volume through an inlet port and is separated by centrifugation in the volume into a lower density components and higher density components. The higher density components are mainly red blood cells, white blood cells and platelets. The lower density component is mainly plasma.

During separation, lower density component is displaced from the volume through an outlet port to a first container. The blood pump is stopped and the collected lower density component is then returned to the separation volume through the inlet port at a second flow rate. The second flow rate is greater than the first flow through a "buffy coat" (made up of white blood cells and platelets), thereby diluting and widening the "buffy coat". The widened "buffy coat" improves the separation between white blood cells and platelets by allowing the denser white blood cells to sediment from the lighter platelets more completely to the outer layers of the buffy coat. In this manner, the separation of the higher density components remaining in the volume is improved. The improved separation between the white blood cells and platelets reduces the amount of white blood cell contamination when the platelets are finally collected.

The lower density component is then recirculated again through the volume at a third flow rate and component with density between lower density component and higher density components (the platelets) are displaced out of the volume while the lower density component is recirculating through the volume at the third flow rate. The third flow rate is at a rate greater than the second flow rate.

Blood components displaced from the volume are monitored by an optical line sensor which determines the specific component being displaced by the optical density of the component. An uninterrupted conduit or passageway is in fluid communication with the outlet port and extends from the outlet port beyond the optical line sensor. The optical line sensor is positioned intermediate the outlet port of the volume and the first container for collecting low density component.

An uninterrupted passageway prevents foam accompanying components displaced from the volume from being mixed more thoroughly with the components, thereby preventing false optical readings by the optical line sensor.

The present invention provides an apheresis apparatus and method for collecting platelet concentrates with lower white blood cell contamination than with existing apparatus and methods while maximizing platelet yields. The lower white blood cell contamination decreases exposure to viruses and possible alloimmunization.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1A:
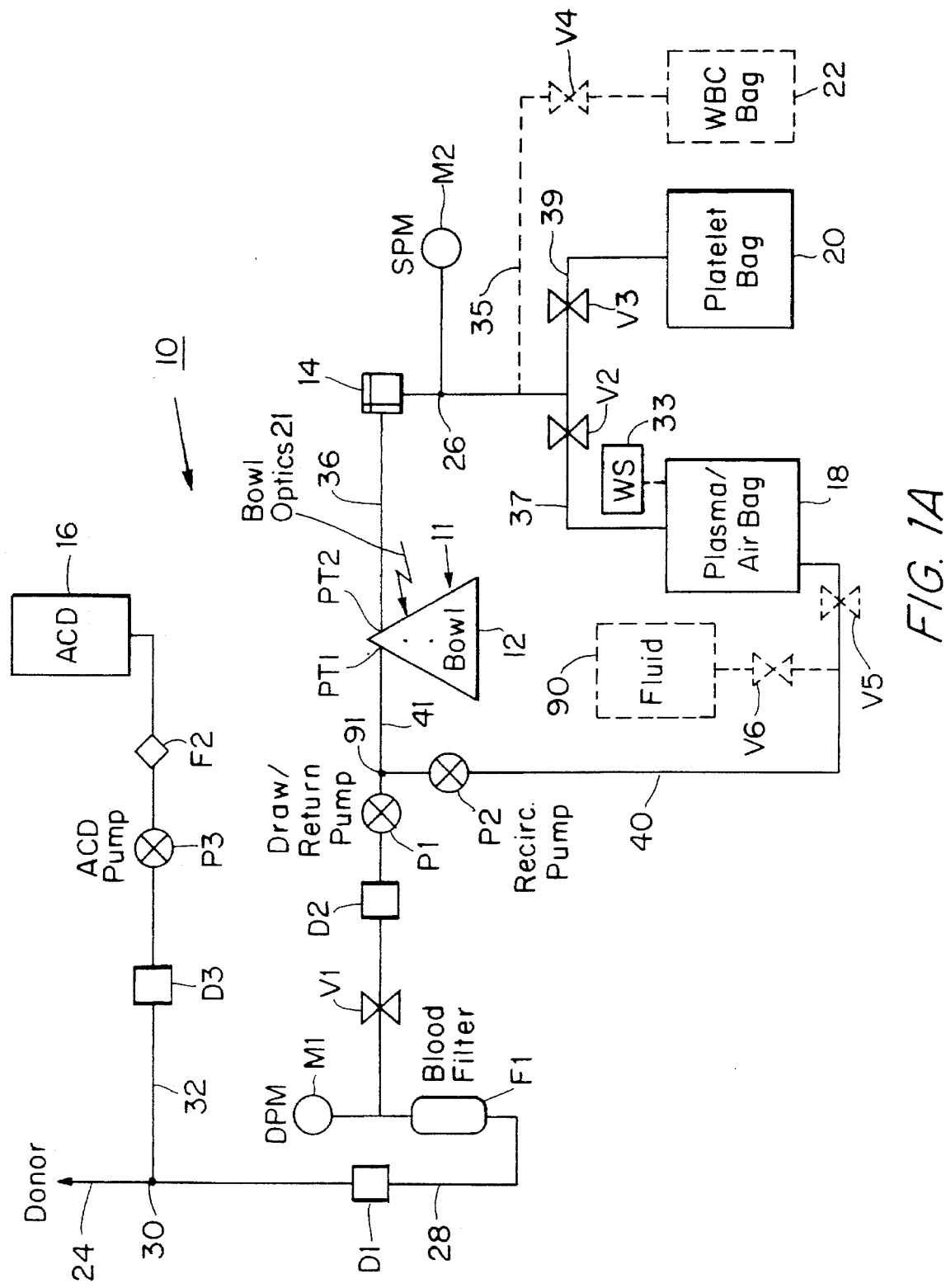
FIG. 1A is a schematic drawing of a preferred embodiment of the apparatus of the present invention.
Figure 1B:
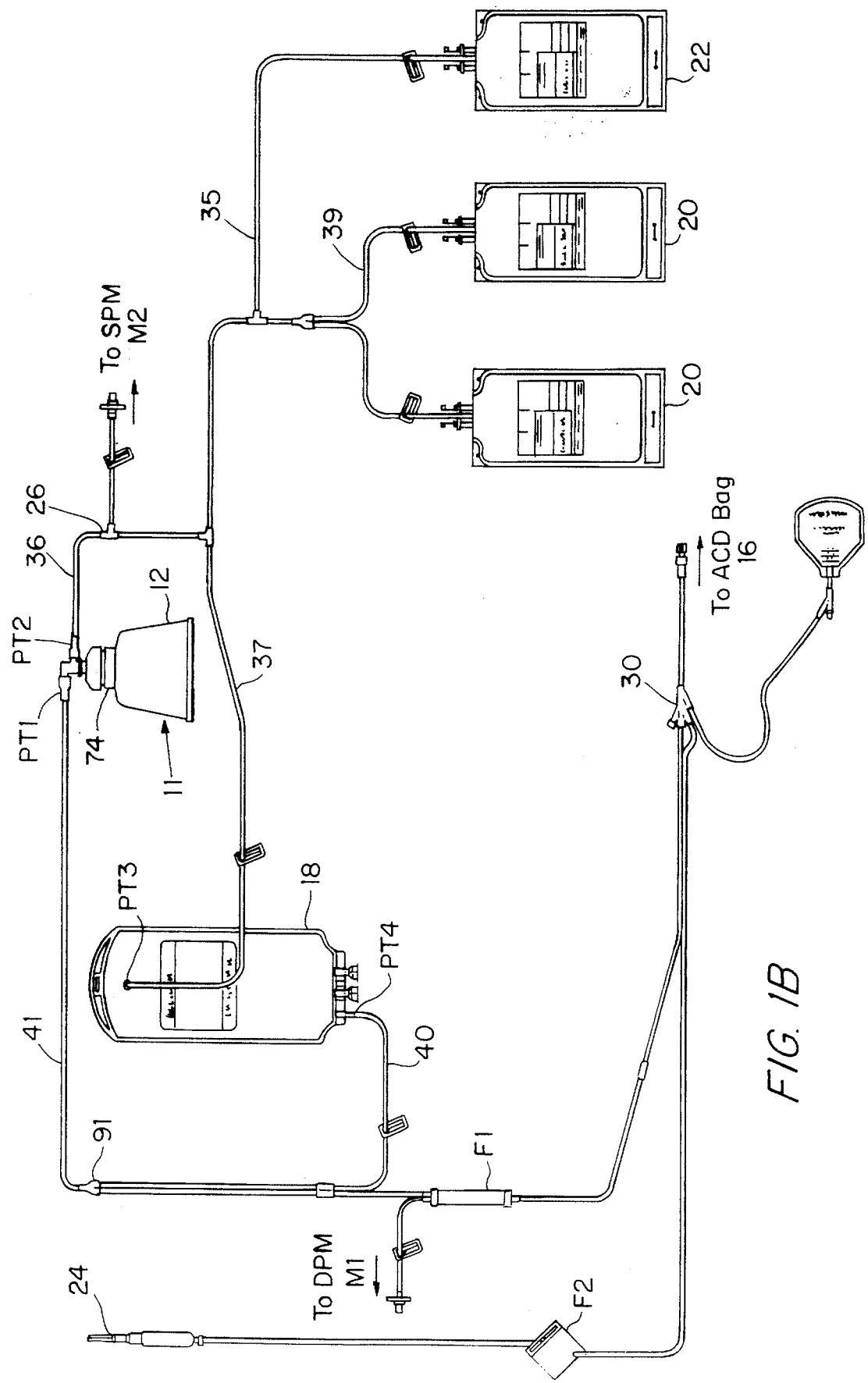
FIG. 1B is a schematic drawing of a disposable system for use with the apparatus of FIG. 1A.

Referring now to FIGS. 1A and 1B, an apheresis system 10 uses a standard Latham type centrifuge 11 similar to the centrifuge described in U.S. Pat. No. 3,145,713 (incorporated herein by reference) for separating anticoagulated whole blood into its constituent components. The centrifuge 11 consists of a rotatable bowl 12 and stationary input and output ports PT1 and PT2 fluidly coupled to the bowl interior by a rotary seal 74 (see FIG. 3). An input port PT1 of centrifuge 11 is in fluid communication with phlebotomy needle 24 via blood filter F1, tubing 28 and Y-connector 30 when valve V1 is open. Tubing 28 is formed of blood compatible tubing as is all the tubing in apparatus 10. An outlet port PT2 of centrifuge 11 is selectively coupled by valve V2 and tubing 36, 37 with a first container 18 labelled plasma/air bag suspended from weight scale 33. A second container 20 labelled platelet bag is selectively coupled via valve V3 and tubing 39, 36 to outlet port PT2.

A third container 16 for storing anticoagulant, is in fluid communication with phlebotomy needle 24 via filter F2, tubing 32 and Y-connector 30. Bacterial filter F2 prevents any bacteria in the anticoagulant (ACD) container 16 from entering the system. Containers 16, 18 and 20 are preferably plastic bags made of blood compatible material. Peristaltic pumps P1, P2 and P3, together with valves V1, V2 and V3, control the direction and duration of flow through apparatus 10 in response to signals generated, by line sensor 14, donor pressure monitor (DPM) M1, system pressure monitor (SPM) M2 and air detectors D1, D2 and D3. Air detectors D1, D2 and D3 detect the absence or presence of fluid. Pressure monitors M1 and M2 monitor pressure levels within apparatus 10. Line sensor 14 is an optical sensor which detects the presence of blood components passing through line sensor 14 from output port PT2.

In initial operation, pumps P1 and P3 are energized to prime tubing 28 of apparatus 10 with anticoagulant from container 16. The anticoagulant passes through filter F2 and Y-connector 30 before reaching air detector D1. Air detector D1 senses the presence of anticoagulant at D1 and terminates the anticoagulant priming operation. During the priming operation, valve V2 is open and sterile air displaced from bowl 12 by the anticoagulant enters the top port PT3 of air/plasma container 18.

Phlebotomy needle 24 is then inserted into the donor and the DRAW stage is commenced. The DRAW stage is the first stage in a sequence of 4 stages; DRAW, DWELL, SURGE and RETURN (see FIG. 2) performed by apparatus 10 when separating blood components. The pump speed for recirculation pump P2 during the DRAW, DWELL, and SURGE stages is graphically shown in curve a of FIG. 2. During DRAW, whole blood is drawn from the donor at a rate of about 80 ml/min and mixed with anticoagulant using pumps P1 and P3. Pump P3 mixes anticoagulant from container 16 with the whole blood drawn from the donor. Valve V1 is open allowing anticoagulated whole blood to pass through tubing 28 and blood filter F1 before being pumped into bowl 12 through inlet port PT1. The whole blood is coupled to the bottom of the bowl 12 through a feed tube (not shown). The ratio of the anticoagulant to whole blood is typically about 1:10.

Figure 3:
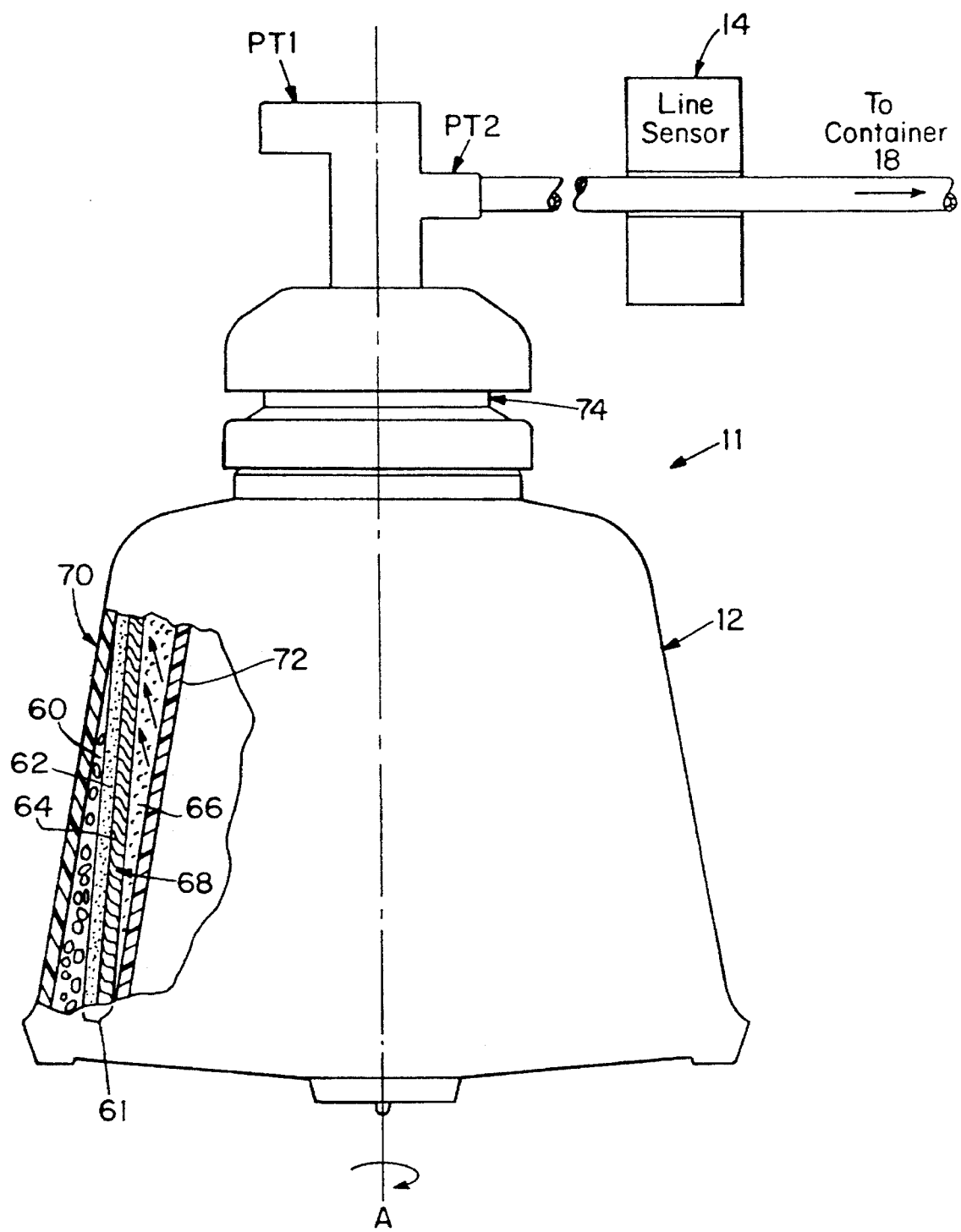
FIG. 3 is a side view of a centrifuge bowl with a section broken away and connected to an optical line sensor 14.

Referring to FIG. 3., centrifuge 11 has a fixed inlet port PT1 and a fixed outlet port PT2. A rotary seal 74 fluidly couples the stationary inlet port PT1 to the lower interior portion of the bowl 12, and the outlet port P2 to an upper portion of the bowl interior for collecting separated fractions. A core 72 occupies a coaxial volume of the interior of bowl 12 and provides a separation volume between the coaxial wall of core 72 and the outer bowl wall 70.

As bowl 12 is rotated, centrifugal forces separate the anticoagulated whole blood admitted into the bottom of the bowl into red blood cells (RBC), white blood cells (WBC), platelets and plasma. The blood is separated into different fractions in accordance with the component densities. The higher density components, i.e. RBCs 60, are forced to the outer wall 70 of bowl 12 while the lighter density plasma 66 lies nearer the core 72. A "buffy coat" 61 is formed between the plasma 66 and the RBCs 60. The "buffy coat" 61 is made up of an inner layer of platelets 64, a transitional layer 68 of platelets and WBCs and an outer layer of WBCs 62. The plasma 66, being the component closest the exit port from the separation volume, is the first fluid component displaced from bowl 12 via port PT2 as additional anticoagulated whole blood enters bowl 12 through port PT1.

Returning to FIG. 1A, the exiting plasma passes through line sensor 14, tubing 36, 3-way T-connector 26 and valve V2 (in the open position) before entering air/plasma container 18. Plasma entering air/plasma bag 18 is drawn from container 18 by recirculate/surge pump P2 and is recirculated at about 20–30 ml/min into bowl 12 through port PT1. The recirculated plasma dilutes the anticoagulated whole blood entering bowl 12 and allows the blood components to separate more readily. The equation for optimum recirculation rate is as follows:

$$Qr = Qc - \left[\left[1 + \left[\frac{Hd}{100}\right] \cdot (ACD - 1)\right]\right] \cdot Qd$$

where,

Qr=recirculation flow rate (ml/min.)

Qc=critical flow rate (ml/min.)

Hd=donor hematocrit (%)

ACD =ACD/anticoagulated whole blood ratio

Qd=Draw flow rate (ml/min.)

A critical flow rate of between 60 and 80 ml/min. has been shown to be effective at keeping platelet separated from WBC's. When a bowl optical sensor 21 senses the "buffy coat" is at a particular radius called the "surge" radius (≈3.81 cm), the DRAW cycle is completed. Valve V1 is closed, pump P1 is stopped so blood is no longer drawn from the donor and the DWELL stage is commenced.

Figure 2:
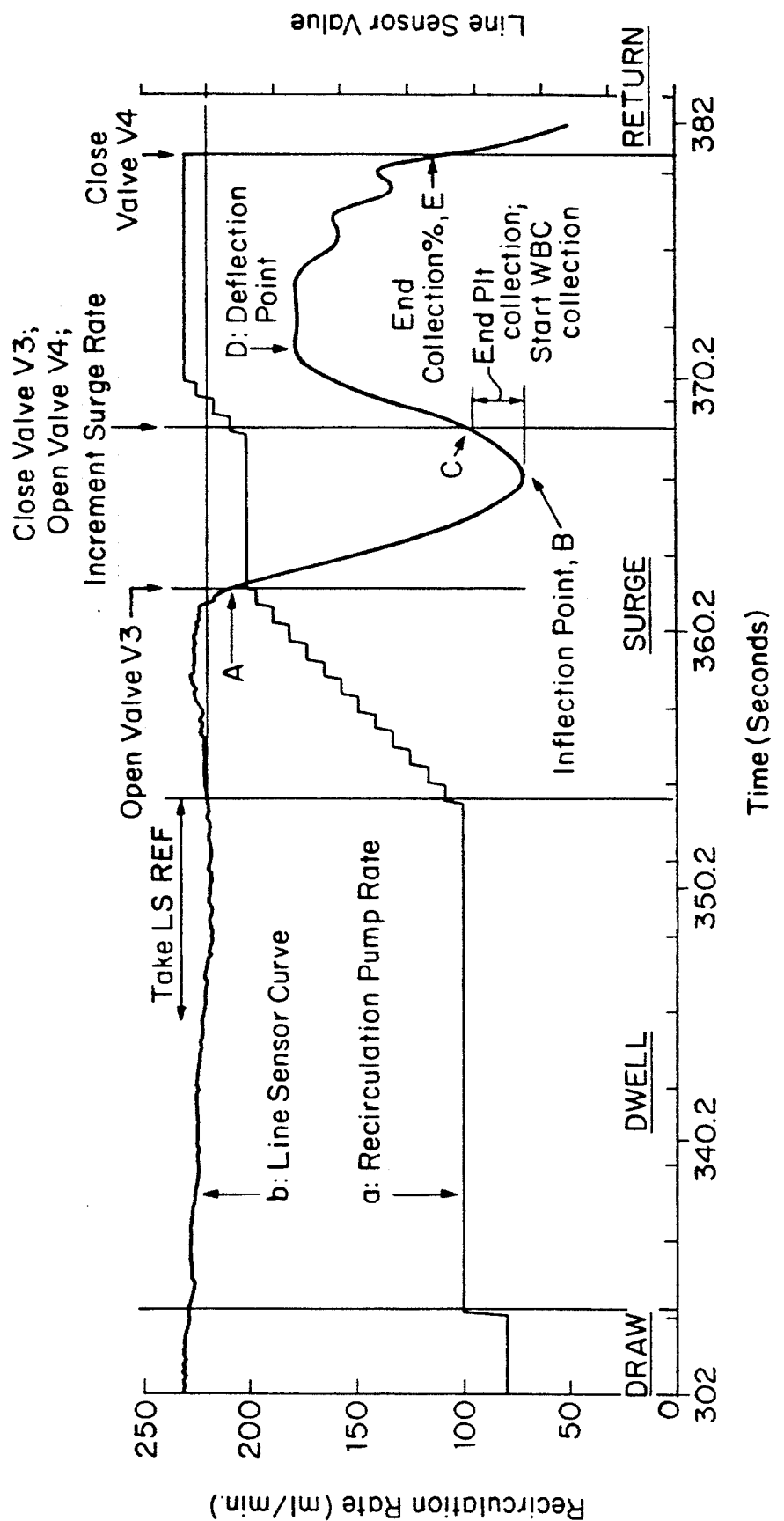
FIG. 2 is a graph showing recirculation pump speed in ml/min (curve a) and line sensor output values (curve b) at different stages of the blood separation process for a three pump apparatus of FIGS. 1A and 1B of the invention.

During DWELL, pump P2 recirculates plasma 66 through bowl 12 at a moderate rate (about 100 ml/min as depicted in FIG. 2) for about 20–25 sec. (331–354). At this flow rate, the "buffy coat" 61 widens but the platelets do not leave bowl 12. The lowered concentration of particles in the "buffy coat" allows the heavier white cells to sediment to the outer side of the "buffy coat". The recirculated plasma maintains a constant flow rate of dilutant through the "buffy coat" (in the direction of the arrows) and results in a better separation between the lighter platelet layer 64 and the heavier white blood cell layer 62. As a result, the transitional layer 68 is reduced. The DWELL period also allows the flow patterns in bowl 12 to stabilize and allows more time for microbubbles to leave bowl 12 and be purged.

After DWELL, the SURGE stage is commenced. In SURGE, the speed of pump P2 (starting at 100 ml/min) is increased in 10 ml/min increments to recirculate plasma until reaching a platelet surge velocity of about 200 ml/min. The platelet surge velocity is the velocity at which platelets can leave bowl 12 but not red blood cells or white blood cells. The plasma exiting the bowl becomes cloudy with platelets and this cloudiness is detected by line sensor 14 (See FIG. 2, curve b) and the output of the detector decreases at point A. Line sensor 14 consists of an LED which emits light through blood components leaving the bowl 12 and a photo detector which receives the light after it passes through the components. The amount of light received by the photo detector is correlated to the density of the fluid passing through the line.

When platelets first start leaving the bowl 12, the line sensor output starts to decrease. At point A in curve b, FIG. 2, valve V3 is opened and valve V2 closed and the platelets are collected in container 20. Once the majority of the platelets are removed, from bowl 12, the fluid exiting the bowl becomes less cloudy. This lessening of cloudiness is detected by line sensor 14 and the line sensor output bottoms out at the inflection point B. At this point the total depth of the curve is taken, and the machine waits until the sensor signal rises for a given percentage, point C. At this point of time, the valve V3 is closed and the collection ended, or collection of white cells initiated.

Optionally, at this point C, collection of WBC may be started as indicated in FIG. 1A, utilizing an additional valve V4 and a third collection container, WBC bag 22 (shown in dotted lines in FIG. 1A). After the line sensor output has reached its minimum, inflection point B, the fluid starts to clear out. Once the sensor output has risen a given percentage, relative to the total depth of the curve, point C is reached and valve V3 is closed, valve V4 is opened and the recirculation pump further increases its speed to the lymphocyte surge rate. This initiates the collection of WBC. The line sensor will soon reach a maximum; the deflection point D. Once the deflection point has been reached, the cloudiness of the fluid will start to increase again as larger particles start to leave the bowl. The machine now waits for the sensor signal to drop to a given percentage of the original line sensor reference value; point E. At this point red cells start leaving the bowl and valve V4 is closed and collection is ended.

After the platelets and/or WBC have been collected, apparatus 10 begins the RETURN stage. During return, the rotation of bowl 12 is stopped and the remaining blood components in bowl 12 are returned to the donor (by reversal of rotation of pump P1) via phlebotomy needle 24 with valve V1 open. V2 is also opened to allow air to enter the centrifuge bowl during return. Plasma from container 18 dilutes the remaining blood components in bowl 12. Pump P2 mixes the plasma with the returning components in bowl 12 with valve V2 open diluting the returned components to speed up the return time. When the remaining blood components in the bowl have been returned to the donor, the RETURN stage is terminated and the phlebotomy needle 24 may be removed from the donor.

Depending upon the amount of platelets needed, this process of DRAW, DWELL, SURGE and RETURN can be performed multiple times.

During DRAW, the anticoagulated whole blood entering bowl 12 can be diluted with a solution such as saline from a container 90 (shown in dotted lines) instead of plasma using V6, V5, and pump P2.

Figure 6:
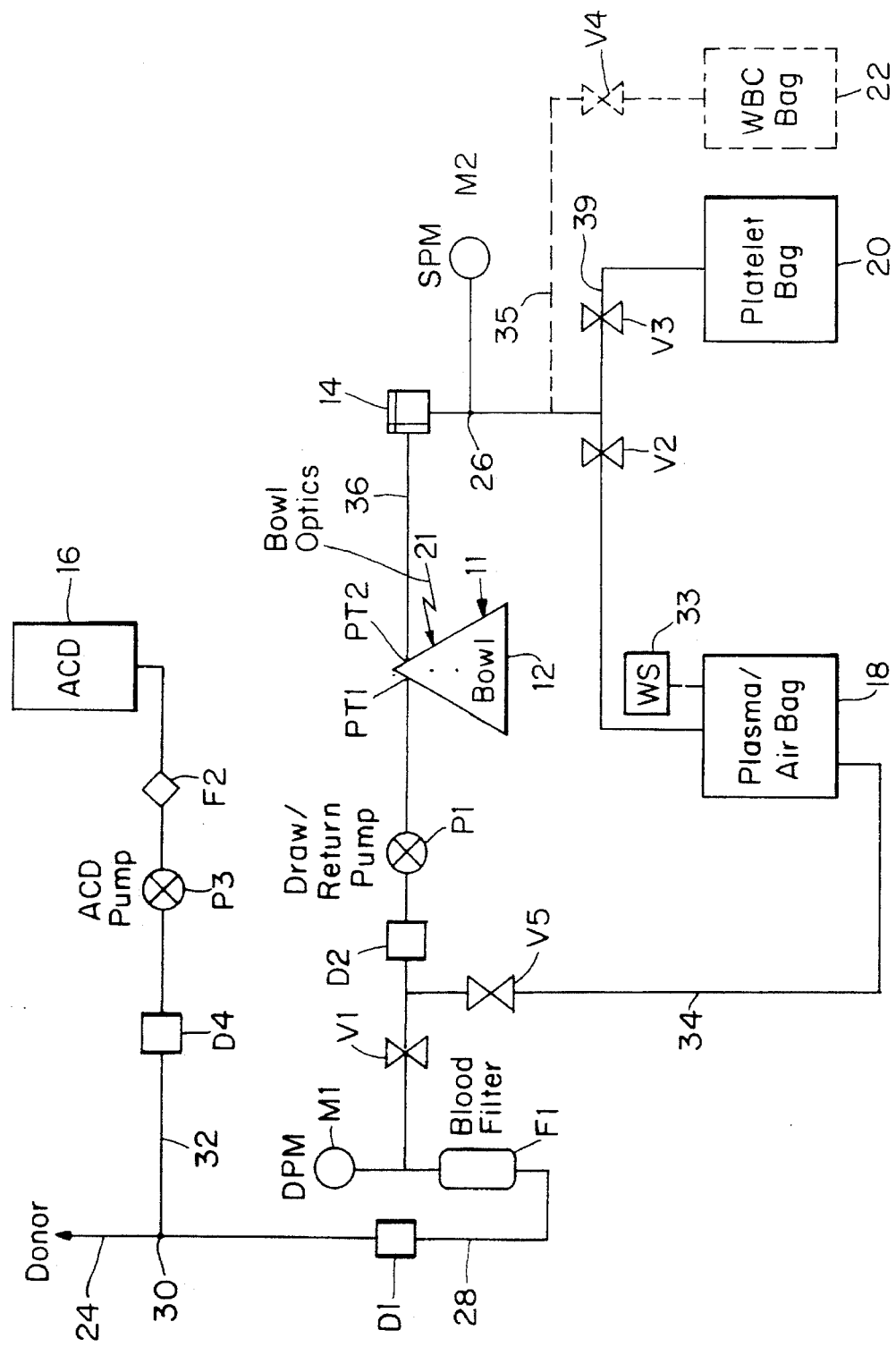
FIG. 6 is a schematic drawing of a two pump preferred embodiment of the present invention.

An alternative two pump embodiment 50 of the present invention is shown schematically in FIG. 6. Apparatus 50 uses two pumps, draw/return pump P1 and an anticoagulant pump P3.

Figure 7:
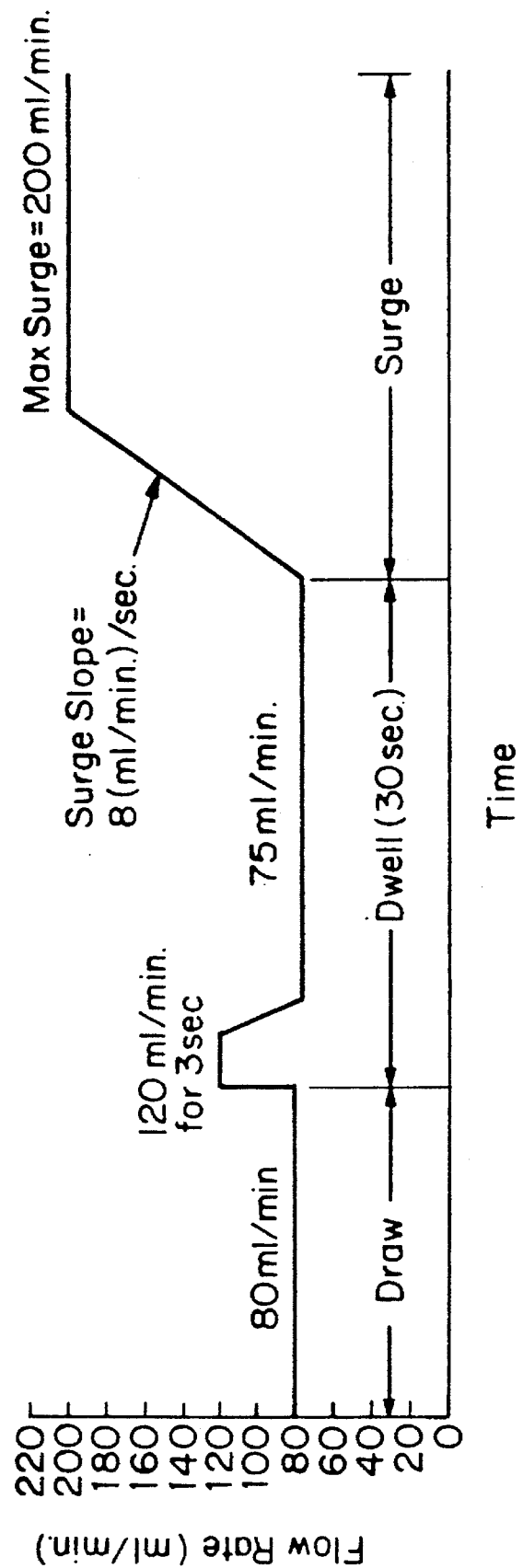
FIG. 7 is a graph Showing pump speeds at different stages of blood separation for a two pump apparatus of the invention.

In operation, apparatus 50 is primed in the same manner as previously discussed. Apparatus 50 also performs the DRAW, DWELL, SURGE and RETURN stages in a similar manner to that of apparatus 10. FIG. 7 graphically shows the pump speeds for pump P1 for the DRAW, DWELL and SURGE stages. During the DRAW stage, whole blood is drawn from a donor and mixed with anticoagulant using pumps P1 and P3. Valve V1 is open, allowing anticoagulated whole blood to pass through tubing 28 and blood filter F1 before being pumped into bowl 12 through inlet port PT1. Bowl 12 is rotated, separating the anticoagulated whole blood into different fractions. The least dense component, i.e. plasma 66, is the first displaced from bowl 12 via port PT2 as additional anticoagulated whole blood enters bowl 12 through port PT1. The plasma passes through tubing 36, is sensed by line sensor 14 and completed through T-connector 26 and through valve V2 (in the open position) and enters container 18. Valve V5 is closed, permitting the plasma to collect in container 18. After the bowl optics 21 sense the "buffy coat" is at the proper position, valve V1 closes, terminating the DRAW stage.

Apparatus 50 then begins the DWELL stage. During DWELL, pump P1 pumps collected plasma from container 18 (with valve V5) open into bowl 12 through tubing 34 and port PT1 at an elevated rate of 120 ml/min for a period of about three seconds before dropping to a moderate 75 ml/min for about 27 more seconds (FIG. 7). The plasma 66 flows through the "buffy coat" and dilutes it. The three second period of elevated flow rate thus widens the thickness of "buffy coat" thereby providing a better separation between platelets and WBCs. The remaining period at the moderate flow rate stabilizes the flow patterns in bowl 12. After DWELL, pump P1 increases the flow rate of the recirculating plasma at the rate of 8 (ml/min)/sec until reaching the maximum surge velocity of 200 ml/min (FIG. 7). At the maximum surge velocity, platelets (FIG. 3) begin to exit bowl 12. The plasma exiting the bowl 12 becomes cloudy with platelets and this cloudiness is detected by line sensor 14. Line sensor 14 causes valve V3 to open and the platelets are collected in container 20. After the platelets have been removed from bowl 12, line sensor 14 detects the absence of platelets and closes valve V3.

Optionally the WBC collection stage can be commenced using values V4 and WBC by 22 (shown in dotted lines) after which the RETURN stage is commenced. The rotation of bowl 12 is slowed and the remaining blood components in bowl 12 are returned to the donor by pump P1 via phlebotomy needle 24.

Figure 4:
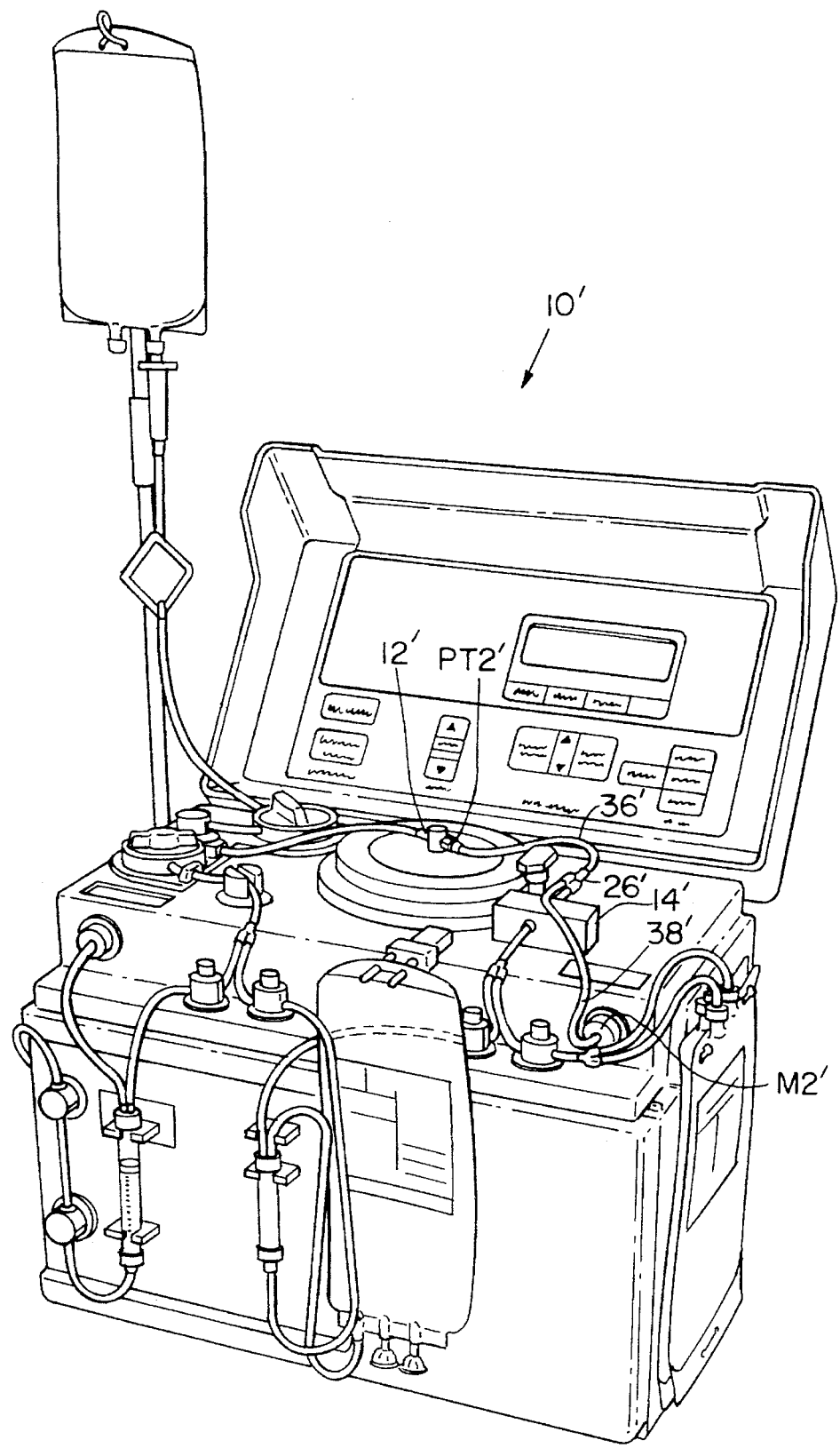
FIG. 4 is a plan view of a prior art apheresis apparatus showing a Y-connector upstream of the optical sensor 14.

FIG. 4 depicts a prior art product sold by Haemonetics Corporation under the name Mobile Collection System (MCS). This system 10' physically is similar to the present system and has the surge capability of the prior out patient referenced supra. In this system the branching connector 26' is located upstream of the optical sensor 14'. Outlet port PT2' is in fluid communication with tubing 36' and Y-connector 26'. One branch of tubing 36' passes through optical sensor 14'. M2' is coupled directly to pressure monitor M2' via tubing 38'. This prior art location of Y-connector 26' causes foam, which is floating on the surface of blood components leaving bowl 12' through port PT2' to substantially mix with the separated components. The mixing of the foam with the components results in false readings from the optical line sensor 14' because the mixed foam scatters light emitted by the LED of line sensor 14' so that the photo detector does not receive the correct amount of light associated with the specific blood component exiting bowl 12'. False reading can cause less than optimal component collection i.e., less platelets are collected than is desired.

Figure 5:
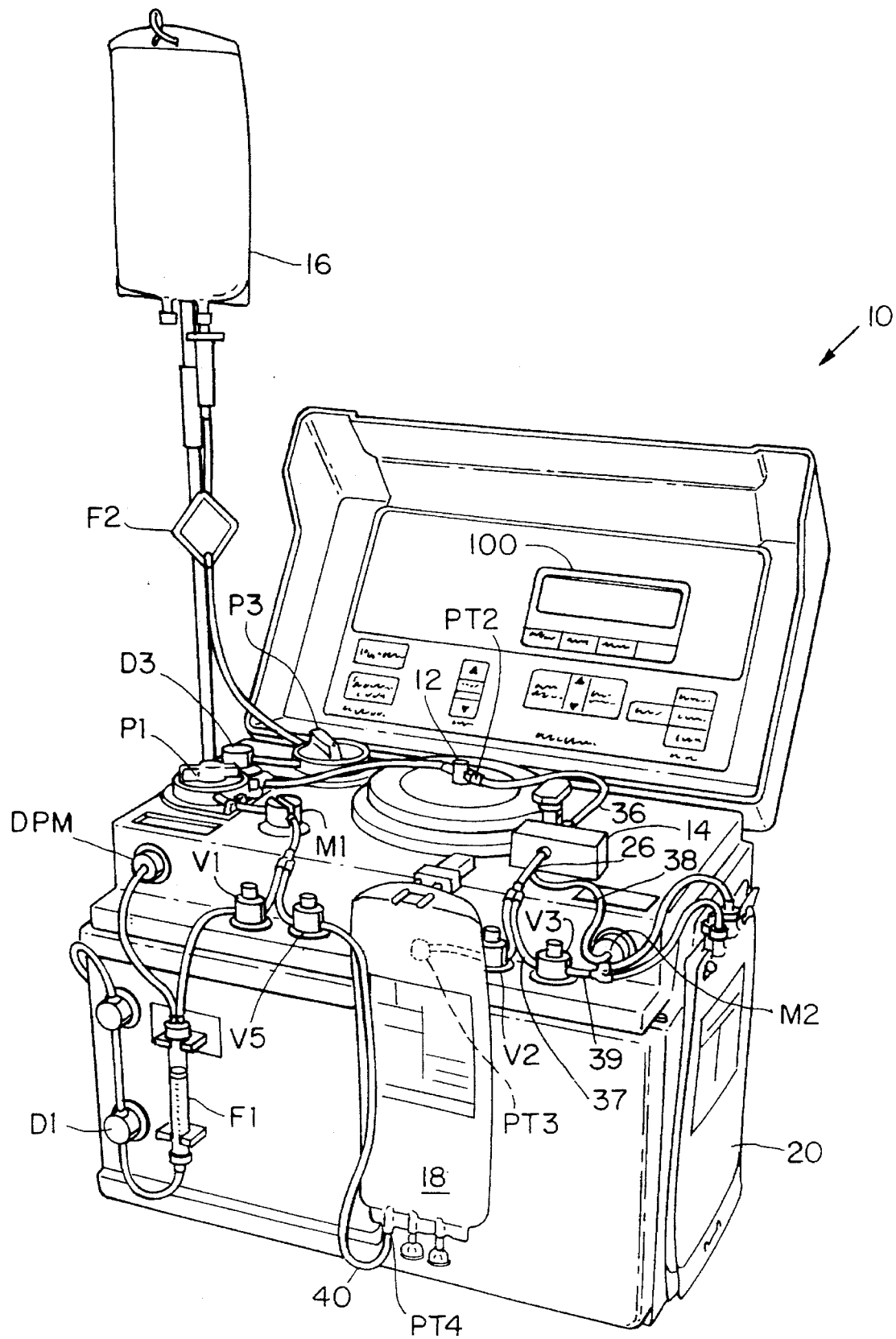
FIG. 5 is a plan view of the present invention showing a T-connector downstream of the optical sensor 14.

FIG. 5 depicts the location of a T-connector 26 downstream of line sensor 14 in the apparatus 10 of the present invention. As may be seen, T-connector 26 is disposed between the line sensor 14 and container 18 and monitor M2 ensuring that an uninterrupted length of tubing 36 is present between port PT2 and the line sensor 14. The uninterrupted tubing 36 reduces the possibility that foam floating on fluid exiting bowl 12 will be substantially mixed with the exiting fluid causing line sensor 14 to make false readings.

Referring back to FIG. 1B and the disposable set depicted therein it should be noted that the length of tubing 36 between PT2 and T-connector 26 must be sufficient to permit T-connector 26 to extend downstream beyond the location of the line sensor 14 (FIG. 5).

Furthermore, use of a so-called "chimney bag" 18 is recommended for the air/plasma application. Chimney bag 18 has a top port PT3 for introduction of air or plasma and a bottom port PT4 coupled via tubing to Y-junction 91 and either to input port PT1 for surge purposes or to phlebotomy needle 24 through filter F1 for fast return purposes. Sterile air from bowl 12 is stored temporarily in the air/plasma bag 18, rather than the conventional use of an air/platelet bag for air storage. By entering the air into the plasma/air bag rather than the platelet bag, the lines 36, 37, 39 and 35 from the bowl 12 to the bags are cleaned out into the plasma bag. This means that any contamination (i.e. WBC's) in the lines will not be drained into the platelet component product. This results in a lower white cell count of the platelet product.

In the DWELL and SURGE stages the chimney bag 18 operates as an air trap; this reduces foaming in the bowl 12 and thus more stable line sensor outputs.

Figure 8A:
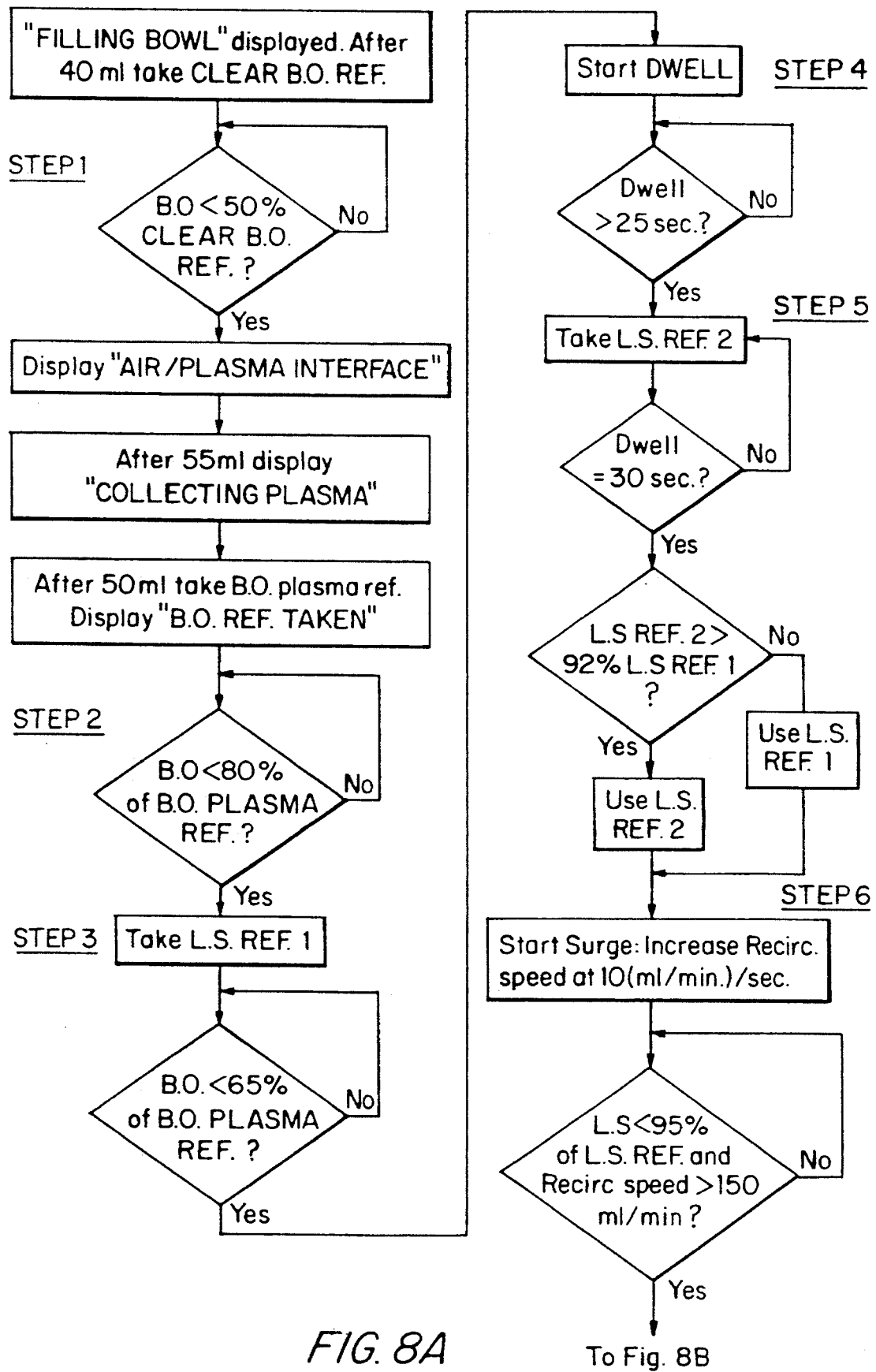
FIGS. 8A and 8B are a processing flow chart of a protocol for a 3-pump embodiment of the invention.
Figure 8B:
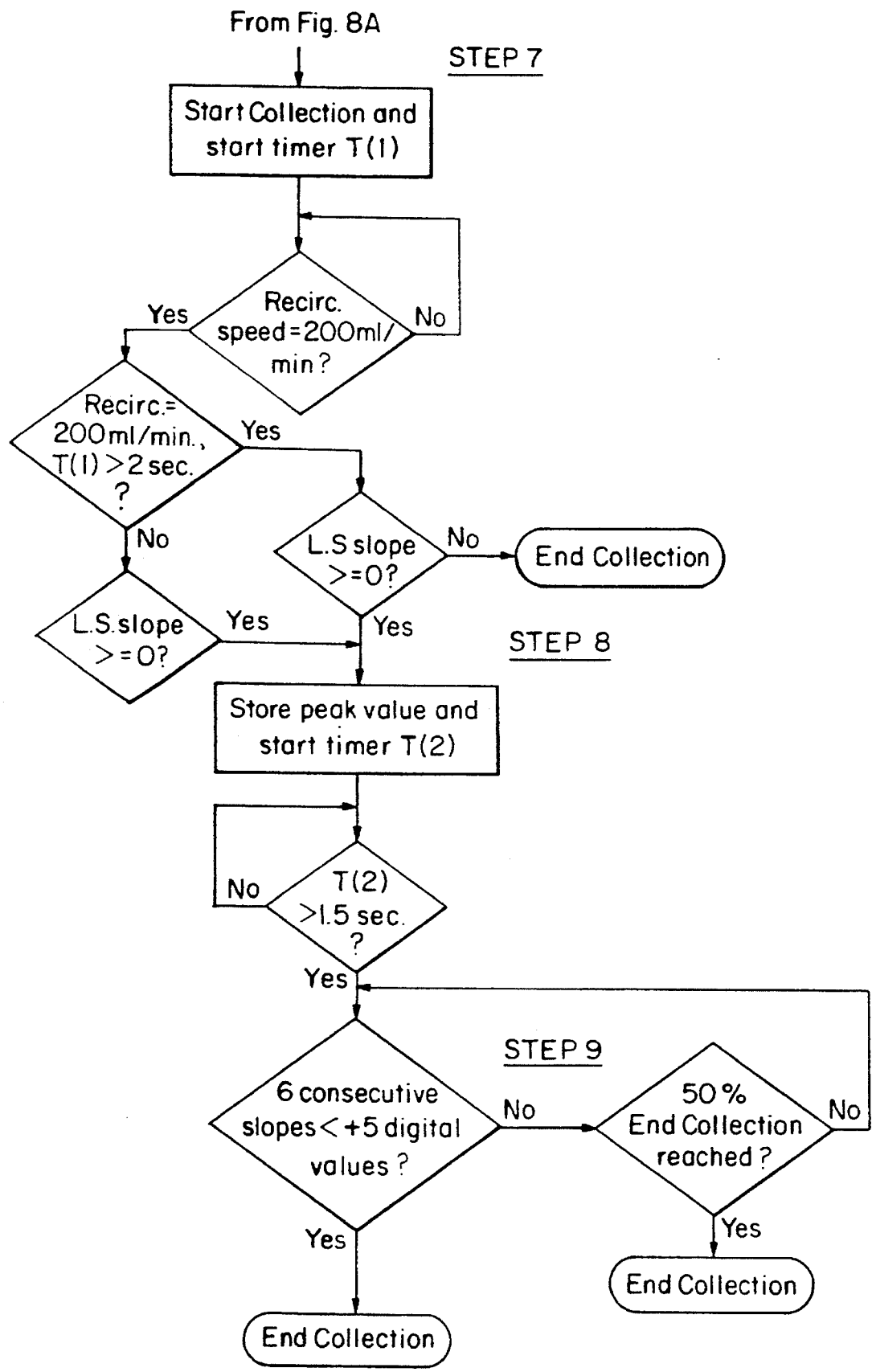

FIGS. 8A and 8B are a processing flow chart indicating the major steps required to process blood and collect platelets in accordance with the apparatus of the invention. In the flow chart the following terms have the meanings given in Table I below:

TABLE I

| Term | Definition |
| --- | --- |
| B.O. | Bowl Optics |
| Ref. | reference |
| L.S. | line sensor |
| Recirc. speed | speed of recirculation pump |
| CLEAR B.O. REF | Bowl optics voltage off empty bowl |
| AIR/PLASMA INTERFACE | Bowl Optics detects fluid |
| COLLECTING PLASMA | Plasma collected through plasma valve |
| B.O. REF. TAKEN | Bowl Optics voltage off plasma in bowl |
| L.S. REF. 1 | Line sensor voltage off plasma taken during Draw cycle |
| DWELL | Draw pump stops. Plasma recirculated at 100 ml/min through bowl |
| L.S. REF. 2 | Line sensor voltage of f plasma taken during DWELL cycle |
| Start Collection | Close plasma valve. Open platelet valve. Start collecting platelets |
| Peak value | Lowest voltage value measured by line sensor |

While the bowl is being filled a display on a control panel (100, FIG. 5) displays "FILLING BOWL" and after 40 ml of anticoagulated whole blood has been pumped by pump P1 into bowl 12 a reading is taken using an optical detector (called the Bowl Optics) located adjacent transparent centrifuge bowl 12. If this reading is less than 50% of an optically clear reference reading with the bowl empty; then the display indicates that fluid has been detected by displaying an AIR/PLASMA Interface signal. If not, a new reading is taken (STEP1).

After another 55 ml has been pumped into the bowl the display indicates that plasma is now being collected and a plasma B.O. reading is taken of the plasma as it forms in the bowl (STEP2). If this reading is less than 80% of a plasma reference reading then a line sensor reading is taken of the plasma during a draw cycle. If not, then step 2 is repeated.

After the line sensor reading is taken (STEP3) another BO reading is taken until the bowl optics reading indicates that the value is less than 65% of the BO plasma reference reading, in which case, the DWELL stage is commenced (STEP4).

After 25 sec. of DWELL a second line sensor reference reading is taken (STEP5). At 30 sec. of DWELL, the line sensor reference 2 value is compared with the line sensor reference 1 value. If L.S. REF 2 is greater than 92% of the L.S. REF 1, then the L.S. REF. 2 value is used as a reference in the next step. If not, then the L.S. REF. 1 value is used (STEP 6).

Next, the SURGE stage is entered by increasing the recirculation speed of Pump P2 in increments of 10 (ml/min)/sec and the line sensor reading is compared with the L.S. REF reading selected in STEP6. If the reading is less than 95% of the reference value and the pump speed is greater than 150 ml/min platelet collection is commenced and timer T(1) is started (STEP 7).

When the recirculation speed is equal to 200 ml/min the speed is kept constant at 200 ml/min. If T(1) is less than or equal to 2 seconds and the slope of the Line Sensor curve (curve b of FIG. 2) is greater than or equal to zero, the peak value of the LS curve is stored and timer T(2) is started. If T(1) is greater than 2 seconds and the LS slope is not greater than or equal to zero, platelet collection is terminated (STEP 8).

Timer T(2) starts and runs until T(2) is equal to 1.5 second. If over 6 sampling intervals the L.S. output increases by less than +5 digital values over each interval then platelet collection is terminated. If not, the collection is ended when 50% of the difference between the line sensor reference voltage and the line sensor minimum voltage is reached (STEP 9).

Figure 9:
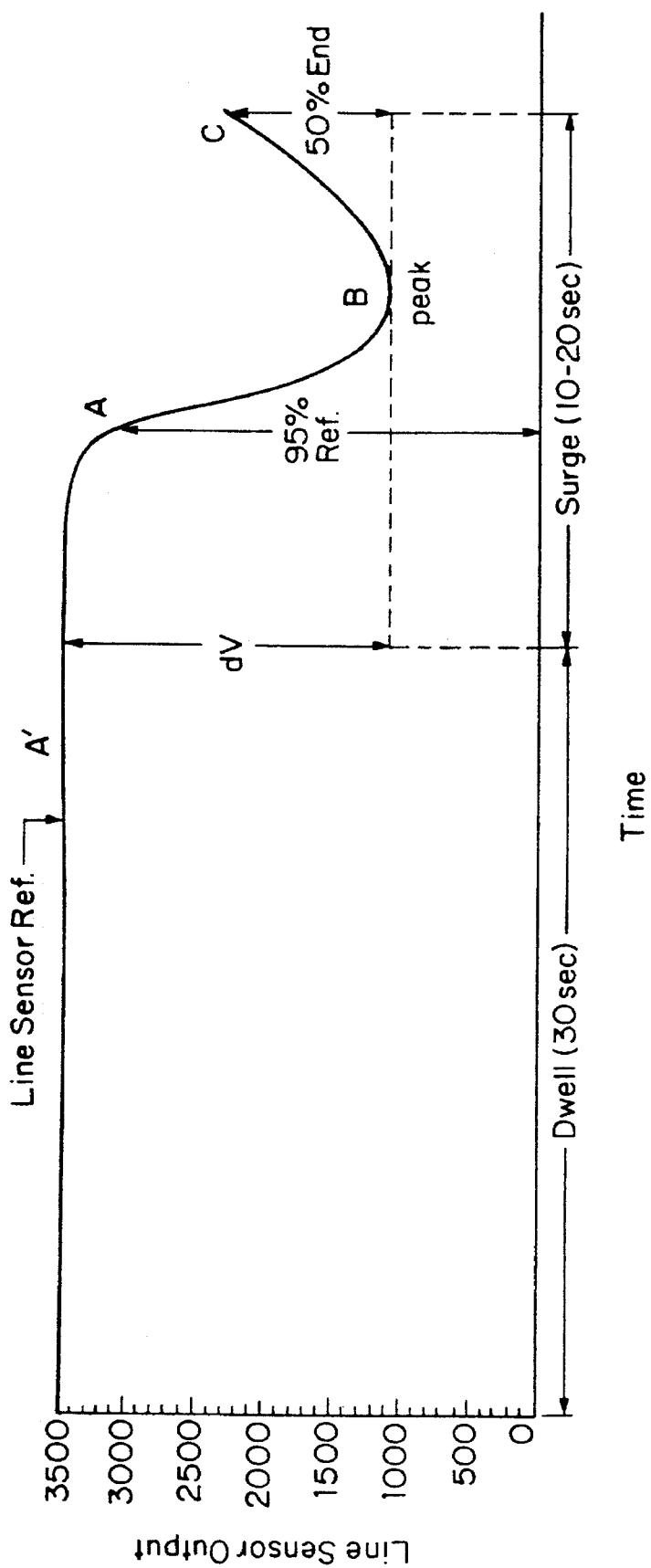
FIG. 9 is a graph showing the output of the line sensor in relation to time during the platelet collection process.

A simplified revision of the line sensor curve b is shown in FIG. 9 to summarize the platelet collection process described above. In FIG. 9 the output of line sensor 14 is plotted versus time for a typical platelet collection process in accordance with the invention. At point A a Line Sensor Reference voltage is taken from the average value calculated at 25–30 sec. into DWELL. Surge is commenced at point B. Platelet collection is commenced when the Surge Speed is greater than 150 ml/min., and the line sensor voltage is less than 95% of the Line Sensor Reference voltage. The slope reversal at point C is detected and the slope is monitored until it levels off or decreases in which case platelet collection is ended. If the slope is increasing then collection is continued until the Line Sensor voltage reaches 50% of the reference value.

While this invention has been particularly shown and described with references to the preferred embodiments thereof, it will be understood by those skilled in the art that various changes in form and details may be made therein without departing from the spirit and scope of the invention as defined by the appended claims.

We claim:

1. A method of increasing intermediate density blood component yield from donated whole blood in a centrifugation fractionation volume, the intermediate density component consisting primarily of at least one of a platelet constituent and a white blood cell constituent, the method comprising the steps of:
   (i) diluting whole blood, by mixing fluid with the whole blood at a first flow rate as the blood is introduced into the volume;
   (ii) separating lower density component in the volume from higher density components in the volume including said intermediate density component, and displacing said lower density component to a first container;
   (iii) recirculating the lower density component to the volume at a second, substantially constant flow rate to further dilute the components remaining in the volume and widen the region occupied by said intermediate density component without causing said intermediate density component to exit the fractionation volume;
   (iv) recirculating the lower density component through the volume at a third, accelerating flow rate; and
   (v) displacing said intermediate density component from the volume while the lower density component is recirculating through the volume at the third flow rate.

2. The method of claim 1 wherein the components remaining in the bowl after (v) are reinfused.

3. The method of claim 1 wherein the second flow rate is greater than the first flow rate.

4. The method of claim 1 wherein the third flow rate is greater than the second flow rate.

5. The method of claim 1 further comprising collecting the intermediate density component in a second container.

6. The method of claim 5 further comprising anticoagulating the whole blood with anticoagulant stored in a third container.

7. The method of claim 6 wherein said intermediate density component consists primarily of platelets and wherein the method further comprises displacing white blood cells from the volume and collecting the white blood cells in a fourth container.

8. The method of claim 1 in which said intermediate density component consists primarily of platelets.

9. The method of claim 1 wherein said intermediate density component consists primarily of white blood cells.

10. The method of claim 1 wherein said intermediate density component consists primarily of platelets and white blood cells.

11. A method of increasing intermediate density component yield from donated whole blood in a centrifuge having an enclosed fractionation volume, the intermediate density component consisting primarily of at least one of a platelet constituent and a white blood cell constituent, the method comprising:
   (i) pumping whole blood into the volume along a first flow route;
   (ii) separating lower density component in the volume from higher density components in the volume including said intermediate density component, and displacing the lower density component to a first container;
   (iii) closing the first flow route and opening a second flow route, and returning the lower density component to the volume at a first, substantially constant flow rate to widen the region occupied by said intermediate density component without causing said intermediate density component to exit the fractionation volume;
   (iv) recirculating the lower density component through the volume at a second, accelerating flow rate; and
   (v) displacing said intermediate density component from the volume while the lower density component is recirculating though the volume at the second flow rate.

12. The method of claim 11 wherein the components remaining in the bowl after (v) are reinfused.

13. The method of claim 11 wherein the second flow rate is greater than the first flow rate over an entire range of acceleration of the second flow rate.

14. The method of claim 11 further comprising collecting the intermediate density component in a second container.

15. The method of claim 14 further comprising anticoagulating the whole blood with anticoagulant stored in a third container.

16. The method of claim 15 wherein the intermediate density component comprises primarily platelets and the method further comprises displacing white blood cells from the volume and collecting the white blood cells in a fourth container.

17. The method of claim 11 in which said intermediate density component consists primarily of platelets.

18. The method of claim 11 wherein the lower density component initially returns to the volume at a flow rate which exceeds the first flow rate before slowing to the first flow rate.

19. The method of claim 11 wherein said intermediate density component consists primarily of white blood cells.

20. The method of claim 11 wherein said intermediate density component consists primarily of platelets and white blood cells.

21. A method of increasing component yield from donated whole blood in a centrifuge having an enclosed fractionation volume, the method comprising:
   (i) pumping into the volume anticoagulated whole blood having components of varying density including an intermediate density component which consists primarily of at least one of a platelet constituent and a white blood cell constituent;
   (ii) separating lower density component in the volume from higher density components including said intermediate density component in the volume and displacing the lower density component to a first container;
   (iii) returning the lower density component to the volume at a first, substantially constant flow rate to dilute components remaining in the volume and widen the region occupied by said intermediate density component without causing said intermediate density component to exit the fractionation volume;
   (iv) recirculating the lower density component through the volume at a second, accelerating flow rate; and
   (v) displacing said intermediate density component from the volume while the lower density component is recirculating through the volume at the second flow rate.

22. The method of claim 21 wherein the components remaining in the bowl after (v) are reinfused.

23. The method of claim 21 further comprising collecting said intermediate density component in a second container.

24. The method of claim 23 further comprising anticoagulating the whole blood with anticoagulant stored in a third container.

25. The method of claim 24 wherein said intermediate density component consists primarily of platelets and the method further comprises displacing white blood cells from the volume and collecting the white blood cells in a fourth container.

26. The method of claim 24 wherein said intermediate density component consists primarily of platelets.

27. The method of claim 24 wherein the lower density component initially returns to the volume at a flow rate which exceeds the first flow rate before slowing to the first flow rate.

28. The method of claim 24 wherein the whole blood is diluted with lower density component recirculating at a low flow rate before reaching the volume, the low rate being less than the first flow rate.

29. The method of claim 21 wherein said intermediate density component consists primarily of white blood cells.

30. The method of claim 21 wherein said intermediate density component consists primarily of platelets and white blood cells. hite blood cells.

* * * * *